(12) United States Patent
Stroïazzo-Mougin et al.

(10) Patent No.: US 8,969,074 B2
(45) Date of Patent: Mar. 3, 2015

(54) ELECTROMAGNETIC BIOACCELERATOR

(75) Inventors: Bernard A. J. Stroïazzo-Mougin, El Campello (ES); Cristian Gomis Catala, El Campello (ES)

(73) Assignee: Bio Fuel Systems, S.L., Alicante (ES)

( * ) Notice: Subject to any disclaimer, the term of this patent is extended or adjusted under 35 U.S.C. 154(b) by 1428 days.

(21) Appl. No.: 12/519,631

(22) PCT Filed: Dec. 14, 2007

(86) PCT No.: PCT/ES2007/000733
§ 371 (c)(1),
(2), (4) Date: Dec. 7, 2009

(87) PCT Pub. No.: WO2008/074906
PCT Pub. Date: Jun. 26, 2008

(65) Prior Publication Data
US 2010/0120095 A1 May 13, 2010

(30) Foreign Application Priority Data
Dec. 18, 2006 (ES) .................................. 200603212

(51) Int. Cl.
*C12M 3/00* (2006.01)
*B01D 53/84* (2006.01)
*C12M 1/00* (2006.01)
*C12M 1/02* (2006.01)
*C12M 1/12* (2006.01)

(52) U.S. Cl.
CPC ............... *B01D 53/84* (2013.01); *C12M 21/02* (2013.01); *C12M 21/12* (2013.01); *C12M 23/58* (2013.01); *C12M 27/00* (2013.01); *C12M 37/00* (2013.01); *C12M 43/00* (2013.01); *B01D 2251/95* (2013.01); *B01D 2257/304* (2013.01); *B01D 2257/404* (2013.01); *B01D 2257/504* (2013.01); *B01D 2257/7022* (2013.01); *Y02C 10/02* (2013.01); *Y02C 20/20* (2013.01); *Y02E 50/343* (2013.01)
USPC .................. 435/289.1; 435/286.1; 435/286.5; 435/286.6; 435/292.1; 435/294.1; 435/308.1; 435/41; 435/72; 435/134

(58) Field of Classification Search
USPC .................................................... 435/292.1
See application file for complete search history.

(56) References Cited

U.S. PATENT DOCUMENTS

| | | | | | |
|---|---|---|---|---|---|
| 3,738,411 | A | * | 6/1973 | Lazar | 159/47.1 |
| 3,813,789 | A | * | 6/1974 | Shelton | 33/503 |
| 4,364,239 | A | * | 12/1982 | Chapelle et al. | 62/235.1 |
| 4,614,598 | A | * | 9/1986 | Zettier et al. | 210/781 |
| 4,724,214 | A | | 2/1988 | Mori | |
| 4,868,123 | A | * | 9/1989 | Berson et al. | 435/286.6 |
| 4,900,678 | A | | 2/1990 | Mori | |
| 5,106,500 | A | * | 4/1992 | Hembree et al. | 210/266 |
| 5,525,301 | A | * | 6/1996 | Newberg et al. | 422/538 |
| 5,627,070 | A | * | 5/1997 | Gruenberg | 435/286.5 |
| 6,509,188 | B1 | * | 1/2003 | Trosch et al. | 435/292.1 |
| 2005/0260553 | A1 | * | 11/2005 | Berzin | 435/3 |

FOREIGN PATENT DOCUMENTS

| | | |
|---|---|---|
| WO | 91/05849 | 5/1991 |
| WO | 98/00559 | 1/1998 |
| WO | 99/61577 | 12/1999 |
| WO | 2005/059087 | 6/2005 |
| WO | 2006/020177 | 2/2006 |

OTHER PUBLICATIONS

Li, Zhi-Yong, et al. "Effects of electromagnetic field on the batch cultivation and nutritional composition of *Spirulina platensis* in an air-lift photobioreactor." *Bioresource Technology* (2007) vol. 98, pp. 700-705.

De La Noue, J., et al. "The Potential of Microalgal Biotechnology: A Review of Production and Uses of Microalgae." *Biotechnology Advances* (1988) vol. 6, No. 4, pp. 725-770.

* cited by examiner

*Primary Examiner* — Allison Fox
*Assistant Examiner* — Susan E Fernandez
(74) *Attorney, Agent, or Firm* — Ladas & Parry LLP

(57) ABSTRACT

The present invention relates to an electromagnetic bioaccelerator for obtaining biomass by simulating environmental marine conditions, comprising at least the following elements: octagonal biomass converters (1), seawater reserve tanks (3), particle filters (4), UV light filters (5), feedback and mixture tanks (6), pressurization feed tanks (8), manometers (9), pressure controllers (10), buffer tanks (11), expansion tanks with a safety valve (12), heat exchangers (13), temperature control thermostats (14), recycled water feedback tanks (15), reinjection pumps (16), centrifuges for separating the biomass from the water (17), desuperheaters (18); control panels (25), recirculation pumps (26), densimeters (27), biomass mechanical extraction systems by means of centrifugation (32) and biomass accumulation tanks (33).

26 Claims, 4 Drawing Sheets

ELECTROMAGNETIC BIOACCELERATOR

TECHNICAL FIELD OF THE INVENTION

The present invention is comprised within the design of electromagnetic bioaccelerators acting in a continuous and closed manner for the production of biomass with a high energy content in fatty acids, hydrocarbons and the like, such as cellulose, silicates, and of other pharmaceutical products of interest, by means of the mass culturing of autotrophic phytoplankton and zooplankton strains.

The invention relates to the technical field of the exploitation of renewable energies by means of the action of phytoplankton and zooplankton organisms, which are the first and second step of the trophic chain (maximum absorption and minimum loss of electromagnetic energy entering the terrestrial ecosystem occurs in the first two steps of the trophic chain), and phytoplankton organisms usually belonging to the following taxonomic families: Chlorophyceae, Bacillariophyceae, Dinophyceae, Cryptophyceae, Chrysophyceae, Haptophyceae, Prasinophyceae, Raphidophyceae, Eustigmatophyceae, and the zooplankton organisms usually belonging to the Copepod, Thaliacea, Cladocera, Rotifera and Decapod families . . . generally the taxonomic families comprising species of the chromophyte division, all of them characterized by being flagellated or nonflagellated single-celled organisms and with a strictly planktonic (holoplanktonic) life phase, or at least one of its phases being planktonic (meroplanktonic).

The species of the group of phytoplankton organisms the use of which is related to the present invention are, in a non-limiting manner: *Dunaliella salina, Tetraselmis* sp, *Isochrysis galbana, Pavlova lutheri, Rhodomonas salina, Phaeodactylum tricornutum, Thalassiosira weissflogii* and *Chaetoceros socialis*.

The massive capture of gases with a greenhouse effect, especially carbon dioxide, is fomented as described above.

STATE OF THE ART

Obtaining biofuels up until now was done using higher plant cultures, usually plants from the phanerogam group or flowering plants (sunflower, palm, dwarf palm, . . . ), and usually on surface of the earth (terrestrial plants).

The obligation for the economic zones to comply with the objectives imposed by the Kyoto protocol on the reduction of $CO_2/SO_2$ emissions and the emission of other gases causing the so-called greenhouse effect and acid rain is forcing countries to search for alternative and renewable fuels to prevent possible penal taxes.

Although the production of solar and wind energy is increasing in some regions, these technologies are very expensive and are not viable in all climatic areas. In these conditions, biofuels have an important role as substitutes of fossil fuels, especially in transport and heating applications.

The production costs of biofuels from plants, such as palm and rapeseed oil have always been a reason for concern. Taking into account the low oil production indexes per hectare, enormous amounts of resources would be needed to reach commercial production. Land and water are two limited resources and it is preferable to use them to produce food products, which are furthermore more profitable for farmers. Intensive fertilization is furthermore an enormous form of land and water pollution. Extensive single crop farming is also one of the main enemies of biodiversity.

A study conducted by the University of California-Berkeley, *Natural Resources Research* Vol 14 No. 1 March 2005 pp. 65-72, demonstrates that a terrestrial plant such as sunflower uses up more energy than it produces; for example to produce 1,000 Kg of sunflower fuel having an energetic power of 9,000,000 Kcal, 19,000,000 million Kcal of energy must be used, which corresponds to $CO_2$ emissions exceeding the emission of a fossil fuel; for example a 135 hp car traveling 100 Km emits a value of 20 Kg of $CO_2$ with a fossil fuel; when a sunflower-based fuel is used, the total combined emission would be 36 Kg of $CO_2$; however when the fuel is based on phytoplankton, the part of $CO_2$ that the algae has absorbed that remains in the form of cellulose or the like gives a negative result of −6 Kg of $CO_2$. It can therefore clearly be seen that there is a need to generate systems which exploit the use of phytoplankton to generate clean energy that does not negatively affect the earth.

Phytoplankton represents a viable solution to the previously discussed problem given that about 50% of the dry mass of single-celled organisms is generally biofuel. In addition, the annual production per hectare of biofuel from phytoplankton is 40 times higher than with the second most cost-effective product, palm oil. A drawback is that the production of phytoplankton oil requires covering vast stretches of land with rather shallow water, as well as introducing large amounts of $CO_2$, an essential element for phytoplankton to produce oil. Natural production systems, such as phytoplankton ponds, have a relatively low cost but the harvesting process is very laborious and therefore expensive. In addition, phytoplankton culturing is carried out in open systems, making it vulnerable to pollution and to problems for cultures, which may lead to total production loss. In this same sense, an advantage of the electromagnetic bioaccelerator described in the present invention is that the system is kept closed and in conditions such that the culture is not contaminated by bacteria, fungi, . . . because in addition to being closed, the culture is enriched by means of nutrients incorporating fungicides and antibiotics, favoring phytoplankton grown in an axenic medium.

Within the field of the design of electromagnetic bioaccelerators for producing biofuels through photosynthetic microorganisms, two types of bioaccelerators could be clearly distinguished: open electromagnetic bioaccelerators, in which a direct exchange of matter between the culture and the air surrounding it is allowed, and closed electromagnetic bioaccelerators, in which this exchange is eliminated by means of the placement of a transparent physical medium allowing the passage of electromagnetic radiation but not the exchange of matter. Open electromagnetic bioaccelerators present many problems derived from the little control of the culturing conditions and possible pollution, so their application is limited due to these drawbacks. However, closed electromagnetic bioaccelerators efficiently reduce these problems by means of greater control of the culturing conditions and possible pollution and can reach a production rate that is 400 times higher than the production rate of sunflower.

Until now no systems similar to the electromagnetic bioaccelerator object of the present invention have been described which incorporate the advantages of being a closed system with a large volume and large diameters, which works continuously, which allows obtaining large amounts of biofuels or byproducts such as naphthas, glycerin, silicon-derived compounds, such as ferrosilicates, which may further obtain thermal and electric energy that does not contaminate given that all the possible residues, such as carbon dioxide ($CO_2$), are recirculated in the system to be used as a nutrient for the phytoplankton, or which recirculates the water used as part of the culture medium so it can be reused, and not only this; they also significantly reduce atmospheric $CO_2$ and therefore the greenhouse effect.

Due to the ability of the electromagnetic bioaccelerator to accelerate phytoplankton reproduction by means of mitosis and its ability to accelerate photosynthesis, very high production rates can be obtained that are almost equivalent to the energetic power of the fossil hydrocarbons without sulfur. The present invention has the ability to recreate an environment that is similar to the sea (light, temperature and pressure) at a depth in which this phytoplankton is cultured and developed natural. An essential feature of the present invention is that the electromagnetic bioaccelerator system regulates the phytoplankton culture conditions, such as the temperature, pressure and light. Thermal regulation of the system is thus made easier, which in turn makes it easier to control phytoplankton populations being cultured, and reducing the energy costs necessary for maintaining the homoeothermic conditions in the culturing system. And as a second feature, it assures the availability of water with no limitation and high infrastructure costs of any kind.

Another advantage of the electromagnetic bioaccelerator is that it is formed such that it has an electric field and a magnetic field, the ultimate purpose of which is to make phytoplankton production be high and to affect the electron exchanged comprised in photosynthesis.

Therefore the present invention describes a novel system including all these features and allowing wide versatility and being very environmental-friendly.

Patent application WO 03/094598 A1 entitled "Photobioreactor and process for biomass production and mitigation of pollutants in flue gases" describes a generic photobioreactor model mainly focused on decontaminating COX, SOx and NOx type gases. It is basically a system working in a discontinuous manner (distinguishing between day/night photoperiod) and is open, its liquid medium not being axenic. It does not control nitrogen and carbon dioxide concentrations for the purpose of increasing biofuel production. It is not designed to work with monospecific or monoclonal algae strains. Its design does not contemplate biofuel production as the main objective, rather it is focused on gas purification. On the other hand, in relation to the photosynthetic organisms it refers to, it does not demand conditions disabling the system and it has no controlled recirculation because the transport is done by a turbulent flow of bubbles; they are also quite unrelated to the marine environment for plankton.

Compared to the present invention object of the patent, a completely novel system is set forth which is based, in contrast, on the following features:

It is completely closed.
It is completely axenic.
It has an electric field and another magnetic field favorably affecting the development of photosynthesis and mitosis. In summary, it is a system which accelerates the natural photosynthesis process and the transformation of electromagnetic energy into biomass.
It works continuously without distinguishing photoperiods.
It works with monospecific and monoclonal strains.
It accepts mixed autotroph-autotroph, autotroph-heterotroph, facultative heterotroph-facultative heterotroph cultures.
It does not accept just any photosynthetic organism, but rather it at least requires that they are not organisms forming biofouling on the inner surface of the electromagnetic bioaccelerator.
It accepts facultative heterotrophs It requires that the phytoplankton species do not form colonies.
It requires that the phytoplankton species do not generate exo-mucilage.
It requires that the cultured species contains at least 5% of fatty acids and at least 5% of hydrocarbons.
It enhances the use of nonflagellated and floating phytoplankton species.
It does not accept just any type of liquids as culture medium, it focuses on freshwater, brackish water and seawater.
It needs conditions equivalent to the sea between 15 and 50 meters deep (pressure, temperature and light).
Its main objective is to obtain metabolic synthesis compounds with energetic properties or with pre-energetic properties essentially aimed at obtaining biofuels.

DESCRIPTION

The present invention relates to an electromagnetic bioaccelerator (FIG. 1) to obtain biofuels, including but not limited to bio-oil, for the fixation of carbon dioxide ($CO_2$), gases with greenhouse effect and other byproducts listed in no order of importance, such as borosilicates, cellulose, omega 3 type fatty acids and byproducts of a pharmaceutical interest.

An electromagnetic bioaccelerator is understood as a system which uses natural elements such as photosynthesis, mitosis and electromagnetism such that phytoplankton is used as a vehicle to capture, transport and transform energy. In summary, it is a system which accelerates the natural photosynthesis process and transformation of electromagnetic energy into biomass.

Bio-oil is understood as an energetic liquid produced by means of converting electromagnetic energy into chemical energy by means of photosynthesis and is concentrated in the phytoplankton biomass that is of the same origin as the fossil fuel, petroleum, but in the present invention the same energetic product has been extracted without being fossilized.

Said electromagnetic bioaccelerator acts in a continuous and closed manner for the production of biofuel and of other products of interest, by means of the mass culturing of autotrophic phytoplankton strains.

It additionally uses a Tichelmann-type flow control system which allows providing equal pressure in any part thereof and thus continuously controls the extraction.

A first aspect of the present invention consists of a system formed by electromagnetic bioaccelerators consisting of at least the following elements:

at least 1 octagon-shaped biomass converter (1) (FIG. 2) for each electromagnetic bioaccelerator (FIG. 1) which can be of three types: circular single chamber, circular concentric double chamber and circular composite containing vertical tubes arranged around a central light well.

At least one electromagnetic bioaccelerator (FIG. 1) formed by at least 1 biomass converter (1).

Each biomass converter (FIG. 2) is arranged such that the assembly of several of them form a beehive or module-type structure (FIG. 3), allowing natural light to pass through the gaps (2a and 2b) created by said octagonal arrangement. The passage of natural light created between the gaps is used as a passage for natural light within each biomass converter (1) (FIG. 1), and the continuous and homogenous light diffusion is thus achieved within the assembly, as would occur under the level of the sea.

The assembly of biomass converters or modules and the rest of the elements forming the system form the electromagnetic bioaccelerator (FIG. 1).

- at least 1 seawater reserve tank (3) for each electromagnetic bioaccelerator.
- at least 1 particle filter (4) for each electromagnetic bioaccelerator.
- at least 1 UV light filter (5) for each electromagnetic bioaccelerator.
- at least 1 feed and mixing tank (6) for each electromagnetic bioaccelerator.
- at least 1 level control float (7) for each feed tank.
- at least 1 pressurization feed pump (8) for each electromagnetic bioaccelerator.
- at least 1 manometer (9) and at least one pressure controller (10) for each electromagnetic bioaccelerator.
- at least 1 buffer tank (11) for each electromagnetic bioaccelerator.
- at least 1 expansion tank with a safety valve (12) for each electromagnetic bioaccelerator.
- at least 1 heat exchanger (13) to maintain the temperature of the culture medium for each electromagnetic bioaccelerator.
- at least 1 temperature control thermostat (14) for each electromagnetic bioaccelerator.
- at least 1 recycled water feedback tank (15) where the water comes from at least 1 centrifuge (17) for each electromagnetic bioaccelerator.
- at least 1 reinjection pump (16) for each electromagnetic bioaccelerator.
- at least 1 centrifuge for separating the biomass from the water (17) for each electromagnetic bioaccelerator.
- at least 1 desuperheater to reduce the carbon dioxide, hereinafter $CO_2$, inlet temperature (18) for each electromagnetic bioaccelerator.
- at least 2 electromagnetic flow control valves (19) for each biomass converter.
- at least 1 electromagnetic biomass extraction valve (20) for each biomass converter (1) and all the valves of the assembly controlled by control sensors and a central coordination system to assure a continuous extraction flow, assuring maximum cell reproduction.
- at least 3 culture medium control sensors (21) for each biomass converter.
- at least 1 oxygen extraction valve (22) for each biomass converter.
- at least 1 hydrogen extraction valve (23) for each biomass converter.
- 100% natural light inlets (2a and 2b) created by the gaps generated by the arrangement of the biomass converters.
- at least 1 artificial lighting lamp (24) for each biomass converter.
- at least 1 control panel (25) for each electromagnetic bioaccelerator.
- at least 1 recirculation pump (26) for each electromagnetic bioaccelerator.
- at least 1 densimeter (27) for each electromagnetic bioaccelerator.
- at least 1 rotational cleaning system (28) for each biomass converter.
- at least 3 carbon dioxide injection valves (29) arranged helically around each biomass converter.
- at least 2 turbulence injection valves (nitrogen and oxygen) (30) arranged helically for each biomass converter.
- at least 1 artificial light lamp regulation and extraction system (31) for each biomass converter.
- at least 1 mechanical biomass extraction system by means of centrifugation (32) for each electromagnetic bioaccelerator.
- at least 1 biomass accumulation tank (33) connected to the centrifuge.
- at least 1 electromagnetic system, formed by an electric field (34) and a magnetic field (35), responsible for accelerating the molecular and electron exchange, for each biomass converter.

The biomass converters are made of a transparent material, preferably PVC, glass, polycarbonate and/or methacrylate and can be three types:
- circular concentric single chamber.
- circular concentric double chamber.
- circular composite containing vertical tubes arranged around a central light well.

In this same sense, circular concentric single chamber biomass converters (FIG. 2) comprise the following elements:
- vertical control access, maintenance and artificial light emission wells, which have a diameter comprised from 20 centimeters to 2 meters and a height comprised from 5 to 30 meters.
- photosynthesis chambers.

The circular concentric double chamber biomass converters (FIG. 2) contain the following element:
- vertical control access, maintenance and artificial light emission wells (24).

The biomass converters (FIG. 2) comprise at least the following elements:
- vertical artificial light control tube (24).
- $CO_2$, injection valves (29)
- ion sprayers (36).
- turbulence injection valves (30).
- electromagnetic flow control valves (19).
- natural light inlets (2a and 2b).
- artificial lighting lamps (24).
- phytoplankton (37) that is present in the culture medium inside the biomass converter.
- culture control sensor (21).
- internal light systems (24).
- gas extraction valves (23 and 22).
- magnetic field-generating magnets (35).
- electric field-generating electrodes (34).
- electromagnetic biomass extraction valves (20).
- rotational cleaning systems (28).
- artificial lighting lamp regulation and extraction systems (31).

In this same sense, the biomass converters (1) (FIG. 2) are characterized in that they comprise two octagonal reservoirs, one arranged in the upper side and the other one in the lower side. The central part of the converters has a diameter that is less than these reservoirs so as to allow the room temperature and light diffusion inside the modules (FIGS. 2 and 3). The arrangement of said reservoirs thus creates the module or beehive shape (FIG. 3), thus generating the gaps (2a and 2b) and a homogenous monolithic light and temperature assembly.

The seawater reserve tanks (3) are cylindrical or polyhedral made of a fiberglass material, having an internal volume comprised within the range of 1 to 20 $m^3$.

The particle filters (4) are preferably of the cellulose fiber, fiberglass and cellulose acetate type, arranged in a series of sieves with a pore size comprised from 50 microns in pore diameter up to 2 microns in pore diameter, the function of which is to prevent the entrance of particles that are different from seawater.

The UV light filters (5) attenuate wavelengths exceeding 700 nm for the purpose of preventing photosynthesis inhibition and therefore a general phytoplankton production decrease.

The feed and mixing tanks (6) are cylindrical or polyhedral made of a transparent material, preferably PVC, polycarbonate and/or methacrylate, having an inner volume comprised in the range of 3 to 14 m$^3$. In this same sense, the feed and mixing tanks contain the mixture of nutrients and gases necessary for the development and culture of the phytoplankton. It also receives the liquid coming from the centrifuge through the reinjection pump (16).

The floats (17) are for controlling the level of the feed tank and actuate the opening of the seawater inlet valve of the reserve tank (3).

The feed and pressurization pumps (8) are centrifugal-type pumps that can work up to a pressure of 10 Kg/cm$^2$.

The pressure controller (10) regulates the operation of the feed pump (8), depending on the desired pressure inside the circuit.

The buffer tank (11) is made of a transparent material, PVC, polycarbonate . . . , the function of which is to compensate for the different product extractions and to compensate for the pressure drops created by the different extractions. It must always have an inner volume equal to the total volume of the biomass converters (1).

The expansion tank with a safety valve (12) is made of a stainless metal with an inner elastic membrane for absorbing of the small pressure and volume variations comprised between 1 and 2% of the total volume of the electromagnetic bioaccelerator.

The heat exchangers (13) serve to maintain the temperature of the system and are laminar flow plate-type exchangers.

The recycled water feedback tank (15) is transparent and made of fiberglass.

The reinjection pumps (16) are centrifugal-type pumps that can work up to a pressure of 10 Kg/cm$^2$.

The centrifuges (17) are rotary plate type centrifuges.

The culture medium control sensors (21) are photometers, pH meters, temperature probes, $CO_2$ probes, $O_2$ probes.

The photometers measure light intensity by means of the photodiode technique and work in the measuring range of 0 to 200 micromoles of photons/m$^2$s with a minimum resolution of 0.5 micromoles of photons/m$^2$s and with an error that is always less than 4% of the measurement. They will have a reading probe and will be monitored such that they allow the opening and closing of the valves sending the product to the centrifuge.

The oxygen extraction valves (22) and hydrogen extraction valves (23) are hydropneumatic-type extraction valves.

The natural light inlets (2a and 2b) are covered with translucent plastic.

The artificial lighting lamps (24) have an intensity of 1 to 50 watts/m$^2$.

The control panels (25) control the injection of the different nutrients, gases, temperature, pH, salinity and conductivity of the culture medium.

The recirculation pump (26) is a centrifugal-type pump.

The rotational cleaning systems (28) are in the form of balls attached by a central wire which, by means of a centrifugal, helical, rotational movement system, progressively runs across the inner walls of the biomass converter (1), maintaining their cleanness.

The $CO_2$ injection valves (29) are communicated with the ion sprayers (36) and are furthermore arranged helically around the biomass converter (1).

The turbulence injection valves (30) are arranged helically for each biomass converter (1).

In mechanical centrifugation extraction systems, the biomass (32) (which contains lipids, carbohydrates, celluloses, hemicelluloses and secondary metabolism products) is separated from the liquid culture medium.

The culture conditions of the phytoplankton present in the biomass converters for conducting photosynthesis are:
  constant temperature in the range of 20 to 25° C.
  solar light intensity from 200 to 900 watts/m$^2$.
  wavelengths in the range of 400 to 700 nm.
  artificial light intensity from 1 to 50 watts/m$^2$.
  the photoperiods depending on the cultured strain are within the following ranges:
    24:0 hours (light/dark).
    16:8 hours (light/dark).
    18:6 hours (light/dark).
    20:4 hours (light/dark).
    12:12 hours (light/dark).
  Salinity:
    Salt water strains: 20‰-40‰.
    Brackish water strains: 8‰-20‰.
    Fresh water strains: 0.2‰-8‰.
  Phytoplankton concentration in the culture medium from 30 million cells/ml to 500 million cells/ml.
  pH from 6.5 to 8.9.
  Pressure of 1 to 5 atmospheres.

The light diffusion would be similar to the diffusion in an aquatic medium after 15 meters in depth.

The organisms used for the present invention are phytoplankton and zooplankton type organisms, the phytoplankton organisms usually belonging to the following taxonomic families: Chlorophyceae, Bacillariophyceae, Dinophyceae, Cryptophyceae, Chrysophyceae, Haptophyceae, Prasinophyceae, Raphidophyceae, Eustigmatophyceae, and the zooplankton organisms usually belonging to the Copepod, Thaliacea, Cladocera, Rotifera and Decapod families . . . generally the taxonomic families comprising species of the chromophyte division, all of them characterized by being flagellated or nonflagellated single-celled organisms and with a strictly planktonic (holoplanktonic) life phase, or at least one of its phases being planktonic (meroplanktonic).

The species of the group of phytoplankton organisms the use of which is related to the present invention are, in a non-limiting manner: *Dunaliella salina, Tetraselmis sp, Isochrysis galbana, Pavlova lutheri, Rhodomonas salina, Phaeodactylum tricornutum, Thalassiosira weissflogii* and *Chaetoceros socialis.*

The initial strains for the biomass converter inoculation will be maintained in microfiltered seawater using 0.45 micron cellulose acetate filters and subsequent 0.20 micron re-filtering, and finally sterilized using UV rays. The culture medium of the converters will be kept sterile and axenic by means of antibiotics and fungicides.

The antibiotics added to the culture are a mixture of penicillin and streptomycin in a range of concentrations from 100 to 300 mg/l each, preferably in a range of concentrations from 150 to 250 mg/l and more preferably at a concentration of 200 mg/l for each of the components of the mixture.

The fungicides added to the culture are a mixture of griseofulvin and nystatin in a range of concentrations from 100 to 300 mg/l each, preferably in a range of concentrations from 150 to 250 mg/l and more preferably at a concentration of 200 mg/l for each of the components of the mixture.

The culture medium used is to sustain biomasses exceeding 100 million cells/ml, being a Guillard-type medium, according to the protocol described by Robert A., Andersen in the book *Algai Culturing Techniques* with ISBN 0-12-088426-7. Edited by Elsevier, 2005, pp. 507-511.

Said medium has been modified by doubling the nitrogen ($N_2$) concentrations for the purpose of exceeding cell concentrations exceeding 125 million cells/ml.

The electromagnetic bioaccelerators will be sterilized by means of washing with a solution of water and hydrochloric acid (HCl) at concentrations of 0.5 to 5% v/v and/or with water and sodium hypochlorite (NaClO) in a v/v mixture of 0.5 to 5%, and it will all be maintained for at least 24 hours submerged in said solution.

According to a second essential aspect of the present invention, the use of the electromagnetic bioaccelerator is to obtain biofuels, to obtain pharmacopeial products such as fatty acids and lutein, to obtain cosmetic products such as glycerin, pigments and emulsifying substances, to obtain industrial products with a high silica content such as borosilicates and ferrosilicates, to obtain fertilizing products, agricultural products, industrial products and livestock products, to obtain celluloses and hemicelluloses, to obtain tannins and astringent compounds, for the fixation of $CO_2$, $CH_4$, $SH_2$, $NO_2$, $NO_3$ and other greenhouse effect gases and any salt derived from the reaction of these gases with the culture medium.

The term nutrients relates to carbon dioxide, hereinafter $CO_2$, NOx, vitamins, antibiotics, fungicides, water, trace elements and orthophosphoric acid.

EMBODIMENT

Figure 1:
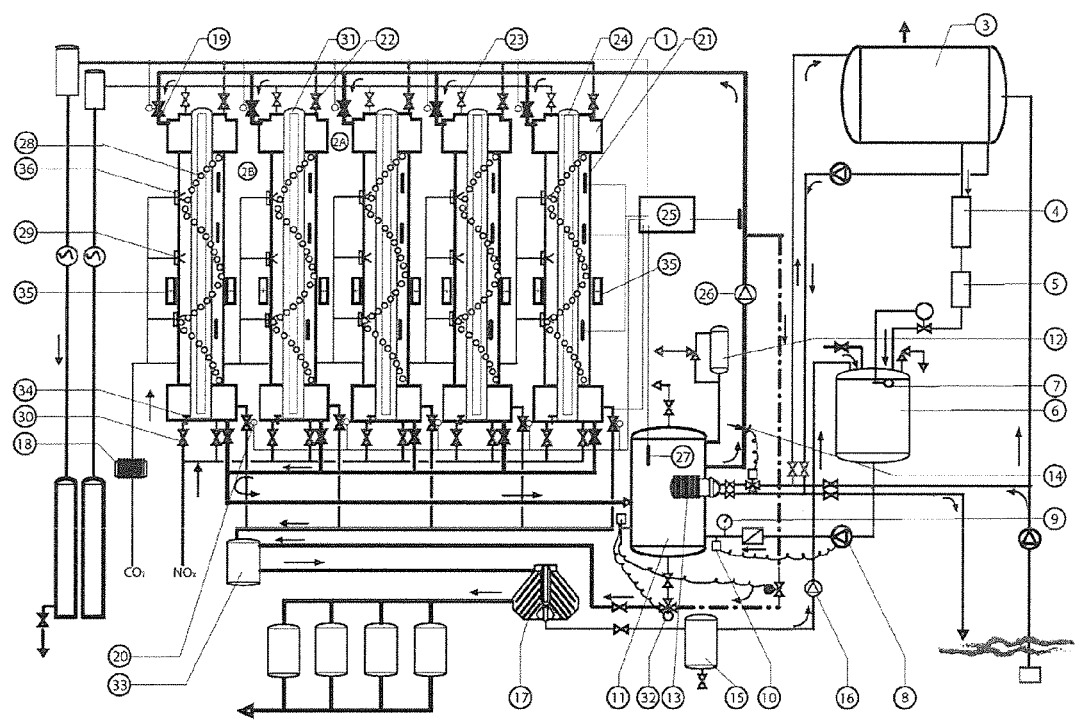
FIG. 1 shows a diagram representing the electromagnetic bioaccelerator object of the present invention with each of its parts and fittings for the use of solar and artificial electromagnetic energy for the purpose of obtaining, among other products, biofuels.
Figure 2:
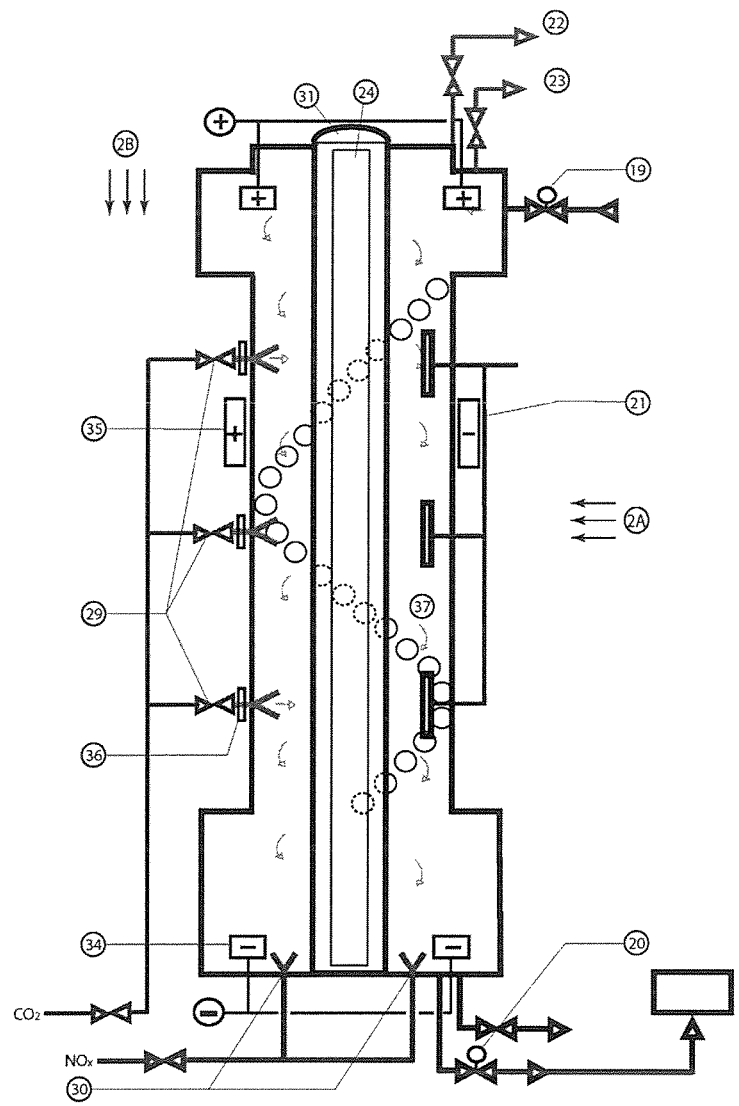
FIG. 2 shows a diagram representing one of the parts of the electromagnetic bioaccelerator, the biomass converters (1), in which photosynthesis and mitosis will be conducted for the production of biomass and elimination of $CO_2$ by the phytoplankton.
Figure 3:
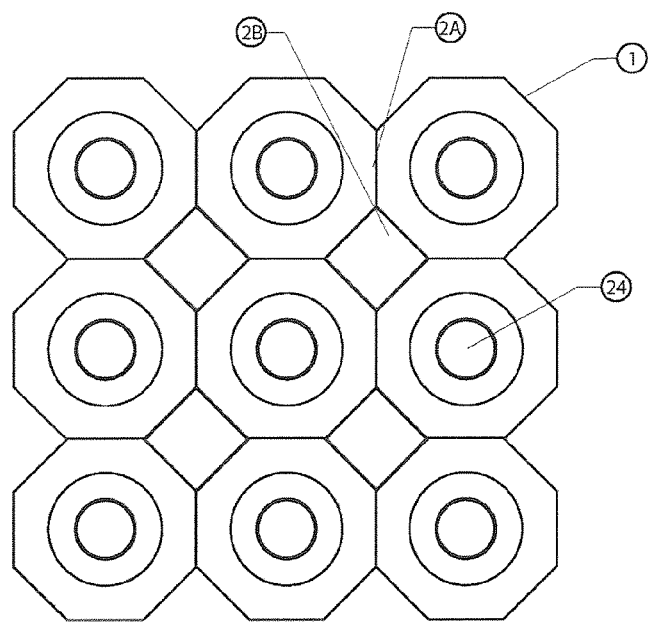
FIG. 3 shows a diagram representing the modular or beehive structure of the biomass converters (1).
Figure 4:
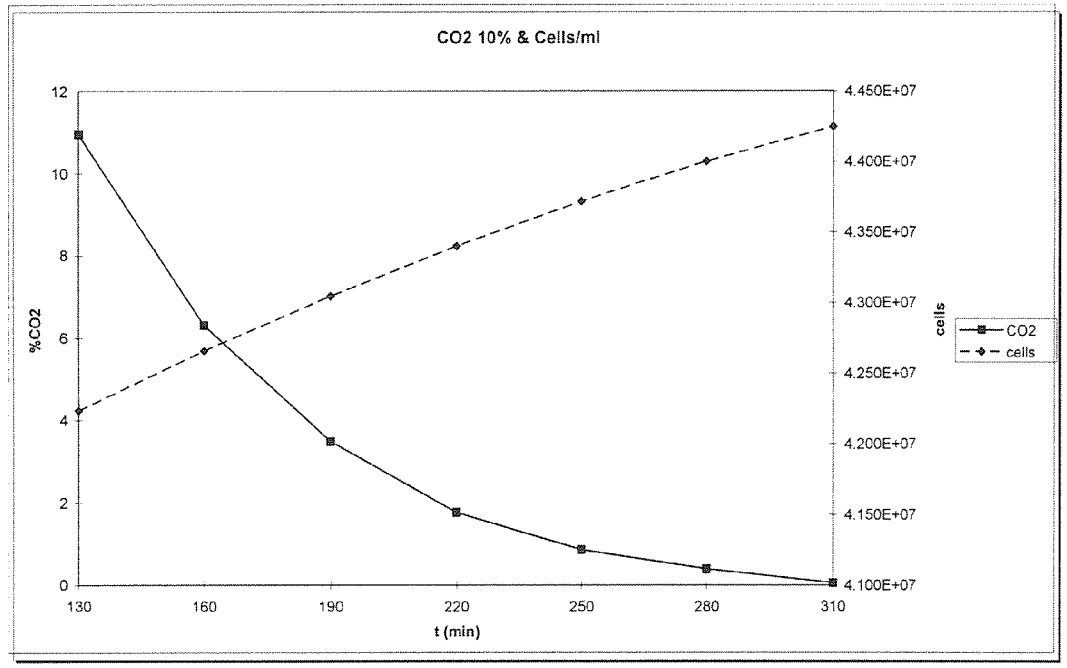
FIG. 4 shows the attenuation of atmospheric $CO_2$ at a concentration of 10% v/v by means of the use of the *Nannochloropsis gaditana* strain.

FIG. 4 shows that by using a culture of 41 million cells/ml in a time interval of 310 minutes, a reduction in an atmosphere rich in $CO_2$ at 10% of all the $CO_2$ existing in said atmosphere was obtained, with a biomass increase of 3.5 million cells/ml. The culture was maintained stable at 22° C. and pH was maintained constant at 8.2. Light was maintained in an 18:6 photoperiod. Experiments conducted in enriched atmospheres at 20% show a similar pattern and direct proportionality to the biomass increase. The species used was *Nannochloropsis gaditana*. The salinity of the medium was 38 per thousand and the experiment was conducted in a closed culture fermenter with a volume of 40 liters.

The initial strains for the biomass converter inoculation are maintained in microfiltered seawater using 0.45 micron cellulose acetate filters and subsequent 0.20 micron re-filtering, and finally sterilized using UV rays. The culture medium of the converters is kept sterile and axenic by means of antibiotics and fungicides.

The antibiotics added to the culture are a mixture of penicillin and streptomycin in a range of concentrations from 100 to 300 mg/l each, preferably in a range of concentrations from 150 to 250 mg/l and more preferably at a concentration of 200 mg/l for each of the components of the mixture.

The fungicides added to the culture are a mixture of griseofulvin and nystatin in a range of concentrations from 100 to 300 mg/l each, preferably in a range of concentrations from 150 to 250 mg/l and more preferably at a concentration of 200 mg/l for each of the components of the mixture.

Figure 5:
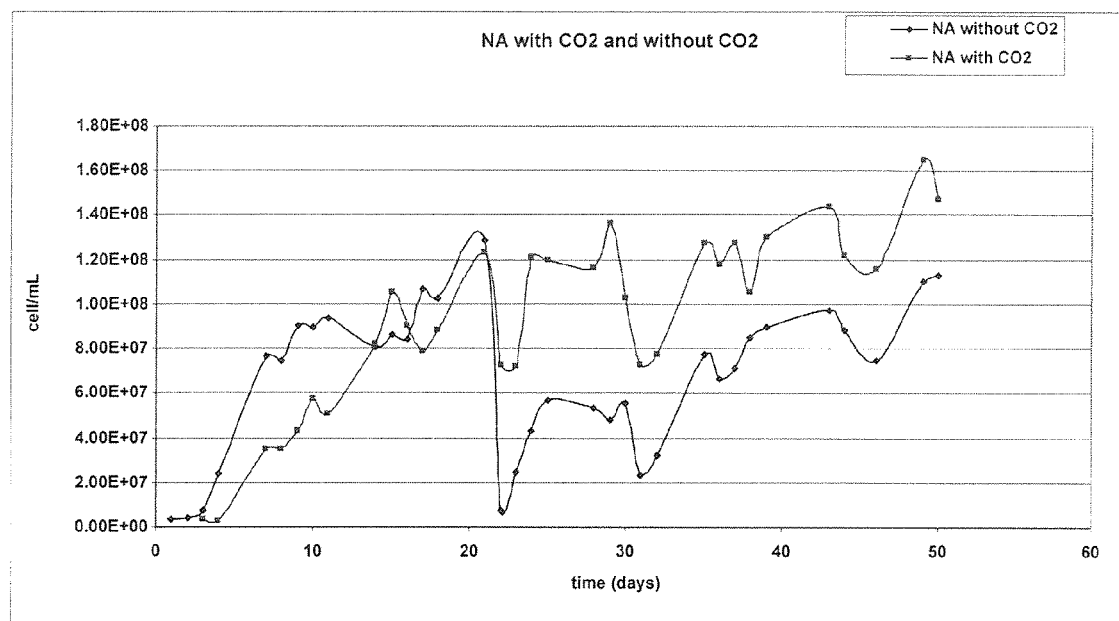
FIG. 5 shows the effect of $CO_2$ on the increase of biomass in a culture of a *Nannochloropsis* sp-type strain, wherein NA represents said type strain.

FIG. 5 shows the difference in the growth of two *Nannochloropsis* sp cultures, the only difference being the presence or absence of air enriched with $CO_2$ at 5%. As can be seen in the figure, growth of the strain with atmospheric air is in the order of 40% less than the growth of the strain cultured with air enriched with in $CO_2$ at 5%. This experiment was conducted in a 0.5 $m^3$ electromagnetic bioaccelerator under temperature, salinity and pH conditions identical to the previous case.

The difference in the efficiency of the strain in the presence and of the strain in the absence of air enriched with in $CO_2$ at 5% becomes especially important once the 120 million cells/ml have been exceeded.

The initial strains for the biomass converter inoculation are maintained in microfiltered seawater using 0.45 micron cellulose acetate filters and subsequent 0.20 micron re-filtering, and finally sterilized using UV rays. The culture medium of the converters is kept sterile and axenic by means of antibiotics and fungicides.

The antibiotics added to the culture are a mixture of penicillin and streptomycin in a range of concentrations from 100 to 300 mg/l each, preferably in a range of concentrations from 150 to 250 mg/l and more preferably at a concentration of 200 mg/l for each of the components of the mixture.

The fungicides added to the culture are a mixture of griseofulvin and nystatin in a range of concentrations from 100 to 300 mg/l each, preferably in a range of concentrations from 150 to 250 mg/l and more preferably at a concentration of 200 mg/l for each of the components of the mixture.

The invention claimed is:

1. A bioaccelerator comprising:
(a) a biomass converter comprising an enclosed chamber having translucent walls that define a cavity within which to contain a plankton containing liquid culture medium, the chamber having an upper octagonal reservoir, a lower octagonal reservoir and a central part disposed between the upper and lower reservoirs, the central part having a circular cross-section and a cross-sectional area less than the cross sectional areas of each of the upper and lower reservoirs whereby an assembly comprising a plurality of the biomass converters can be disposed in a beehive or module arrangement with upper octagonal reservoirs of adjacent biomass converters in contact and with lower octagonal reservoirs of adjacent biomass converters in contact to form gaps between the biomass converters through which light can pass to achieve continuous and homogenous light diffusion in each of the plurality of biomass converters of the assembly;
(b) an inlet for inflow of culture medium into the chamber;
(c) an inlet for inflow of carbon dioxide gas into the chamber; and (d) an outlet from which to discharge biomass from the chamber whereby, in use, plankton contained within the chamber can convert carbon dioxide gas into biomass by photosynthesis.

2. The bioaccelerator according to claim 1, further comprising a central light well that extends from an upper end of the biomass converter downwardly into the chamber.

3. The bioaccelerator according to claim 2, further comprising an artificial lamp disposed within the light well.

4. The bioaccelerator according to claim 1, further comprising means for generating an electric field within the culture medium.

5. The bioaccelerator according to claim 4, further comprising means for inducing a magnetic field within the culture medium.

6. The bioaccelerator according to claim 1, further comprising injectors for injecting gas into the chamber to create turbulent flow within the culture medium contained in the chamber.

7. The bioaccelerator according to claim 6, wherein the injectors are helically disposed about the chamber.

8. The bioaccelerator according to claim 1, further comprising one or more valves for discharge of gas produced by the photosynthesis process.

9. The bioaccelerator according to claim 1, further comprising a cleaning system for cleaning internal surfaces of the translucent walls.

10. The bioaccelerator according to claim 9, wherein the cleaning system comprises a member that rotates within the chamber and contacts the walls of the central part to maintain cleanliness.

11. The bioaccelerator according to claim 1, wherein the inlet for inflow of carbon dioxide gas includes an ion sprayer to ionize carbon dioxide gas for discharge into the chamber.

12. An assembly comprising a plurality of the bioaccelerators of claim 1, the plurality of bioaccelerators being disposed with respect to each other in a beehive or module arrangement with upper octagonal reservoirs of adjacent biomass converters in contact and with lower octagonal reservoirs of adjacent converters in contact whereby to provide gaps between respective biomass converters through which light can pass to achieve continuous and homogenous light diffusion in the plurality of bioaccelerators of the assembly.

13. The assembly according to claim 12, wherein the source of liquid culture medium includes a feed and mixing tank within which filtered water can be mixed with nutrients or gases for development of a plankton-containing culture medium.

14. The assembly according to claim 12, further comprising means to reduce the temperature of the carbon dioxide gas prior to delivery to the carbon dioxide inlet.

15. The assembly according to claim 12, further comprising a control system for controlling any one or more of: conditions of the liquid culture medium within the chamber of each of the plurality of bioaccelerators; inflow of culture medium into the chamber of each of the plurality of bioaccelerators; and inflow of carbon dioxide into the chamber of each of the plurality of bioaccelerators.

16. A method for producing biofuels which comprises cultivating phytoplankton or zooplankton in the bioaccelerator as claimed in claim 1.

17. A method for producing pharmaceutical products which comprises cultivating phytoplankton or zooplankton in the bioaccelerator as claimed in claim 1.

18. A method according to claim 17, wherein the pharmaceutical products are selected from fatty acids and lutein.

19. A method for producing a cosmetic product which comprises cultivating phytoplankton or zooplankton in the bioaccelerator as claimed in claim 1.

20. A method according to claim 19, wherein the cosmetic product is selected from glycerin, pigments and emulsifying substances.

21. A method for producing an industrial product with a silica content which comprises cultivating phytoplankton or zooplankton in the bioaccelerator as claimed in claim 1.

22. A method according to claim 21, wherein the industrial product is selected from borosilicates and ferrosilicates.

23. A method for producing fertilizing products, agricultural products, industrial products and livestock products which comprises cultivating phytoplankton or zooplankton in the bioaccelerator as claimed in claim 1.

24. A method for producing a cellulose or hemicellulose which comprises cultivating phytoplankton or zooplankton in the bioaccelerator as claimed in claim 1.

25. A method for producing tannins and astringent compounds which comprises cultivating phytoplankton or zooplankton in the bioaccelerator as claimed in claim 1.

26. A method for fixation of $CO_2$, $CH_4$, $SH_2$, $NO_2$, $NO_3$ and other greenhouse effect gases, and any salt derived from the reaction of these gases with a culture medium which comprises cultivating phytoplankton or zooplankton in the culture medium in the bioaccelerator as claimed in claim 1.

* * * * *